(12) United States Patent
DelCastilio et al.

(10) Patent No.: US 8,264,363 B2
(45) Date of Patent: Sep. 11, 2012

(54) SYSTEM AND METHOD FOR DETECTING OCCLUSION USING FLOW SENSOR OUTPUT

(75) Inventors: Jorge A. DelCastilio, Des Plaines, IL (US); Atif Yardimci, Vernon Hills, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/016,370

(22) Filed: Jan. 28, 2011

(65) Prior Publication Data

US 2011/0137241 A1 Jun. 9, 2011

Related U.S. Application Data

(62) Division of application No. 11/971,048, filed on Jan. 8, 2008, now Pat. No. 7,880,624.

(51) Int. Cl.
*G08B 21/00* (2006.01)

(52) U.S. Cl. ......................................... 340/608; 600/526

(58) Field of Classification Search .................. 340/608; 600/526, 500
See application file for complete search history.

(56) References Cited

U.S. PATENT DOCUMENTS

| | | |
|---|---|---|
| 4,617,937 A | 10/1986 | Peel et al. |
| 4,648,869 A | 3/1987 | Bobo, Jr. |
| 4,710,163 A | 12/1987 | Butterfield |
| 4,718,896 A | 1/1988 | Arndt et al. |
| 4,979,940 A | 12/1990 | Bobo, Jr. et al. |
| 5,146,414 A | 9/1992 | McKown et al. |
| 5,328,960 A | 7/1994 | Loveless |
| 5,439,001 A | 8/1995 | Butterfield et al. |
| 5,615,671 A | 4/1997 | Schoonen et al. |
| 5,680,109 A | 10/1997 | Lowe et al. |
| 6,280,408 B1 | 8/2001 | Sipin |
| 6,299,583 B1 | 10/2001 | Eggers et al. |
| 6,497,680 B1 | 12/2002 | Holst et al. |
| 6,611,769 B2 | 8/2003 | Olson |
| 6,691,724 B2 | 2/2004 | Ford |

(Continued)

FOREIGN PATENT DOCUMENTS

EP 0 229 354 7/1987

OTHER PUBLICATIONS

International Search Report and Written Opinion dated Nov. 12, 2009.

*Primary Examiner* — John A Tweel, Jr.
(74) *Attorney, Agent, or Firm* — K&L Gates LLP (57) ABSTRACT

A method of detecting an occlusion for an infusion therapy in one embodiment includes: monitoring an output signal from a flowrate sensor for a pulsatile fluid flow having a frequency range, the pulsatile flow being through a fluid pathway to a patient; acquiring a data set that includes the output signal as a function of time; filtering the data set with a noise rejection filter to produce a filtered data set; performing spectra analysis on the filtered data set to determine a strength of the output signal in a frequency domain; calculating a signal strength for the frequency range using the strength of the output signal in the frequency domain; and comparing the signal strength of the range to at least one threshold level to determine if an occlusion is present during the infusion therapy.

11 Claims, 5 Drawing Sheets

U.S. PATENT DOCUMENTS

| | | |
|---|---|---|
| 6,842,117 B2 | 1/2005 | Keown |
| 7,029,444 B2 | 4/2006 | Shin et al. |
| 7,349,813 B2 | 3/2008 | Gutierrez et al. |
| 7,880,624 B2 * | 2/2011 | DelCastilio et al. .......... 340/608 |
| 2001/0010496 A1 | 8/2001 | Shimanuki et al. |
| 2002/0005785 A1 | 1/2002 | Ohmi et al. |
| 2003/0236489 A1 | 12/2003 | Jacobson et al. |
| 2005/0004418 A1 | 1/2005 | Morello |
| 2005/0240289 A1 | 10/2005 | Hoyte et al. |
| 2005/0277912 A1 | 12/2005 | John |
| 2006/0135907 A1 | 6/2006 | Remde et al. |
| 2007/0062251 A1 | 3/2007 | Anez |
| 2008/0047358 A1 | 2/2008 | Petroff |
| 2008/0088464 A1 | 4/2008 | Gutierrez |
| 2008/0189067 A1 | 8/2008 | Duffill et al. |
| 2008/0208527 A1 | 8/2008 | Kavaklioglu |
| 2008/0275349 A1 | 11/2008 | Halperin et al. |

* cited by examiner

SYSTEM AND METHOD FOR DETECTING OCCLUSION USING FLOW SENSOR OUTPUT

PRIORITY CLAIM

This application is a divisional application of and claims the benefit of and priority to U.S. application of patent application Ser. No. 11/971,048 filed Jan. 8, 2008, the entire contents of which are expressly incorporated herein by reference.

BACKGROUND

The present disclosure generally relates to methods and devices for detecting abnormal fluid flow through an infusion system. In particular, the present disclosure is related to devices and methods for detecting occlusions within an infusion system.

Liquid medicaments and other complex medical and therapeutic fluids are often administered to patients through infusion systems. A typical infusion system includes a fluid supply, an infusion flow control device and a fluid pathway. The infusion pathway typically includes one or more sections of fluid lines made of flexible tubing that define a fluid flow path from the fluid supply to a device that administers the fluid to the patient, such as a cannula, needle or catheter. During operation of the infusion system, the infusion control device pushes or forces liquid from the fluid source through the fluid pathway and the administering device into the patient.

One of the problems that can arise during infusion therapy is an occlusion or blockage which completely blocks or severely limits the flow of fluid through the infusions system. Occlusions are undesirable because they can impair the therapeutic effect of a medication being infused. For example, in some infusion therapy applications the liquid medicament is required to be delivered at a specific fluid flowrate for the medicament to be therapeutically effective. In these instances, an undetected occlusion, causing a decrease in flowrate, can diminish the therapeutic effect of the infusion therapy.

Additionally, in any infusion therapy application, an undetected occlusion can cause unnecessary delays in the infusion procedure. For instance, if an occlusion is undetected for a relatively long period of time, the time that passes while the occlusion is undetected increases the time required for the infusion therapy. Thus, in order to avoid complications and unnecessary delays in the infusion therapy, it is beneficial to be able to detect occlusions as soon as possible.

Because an occlusion causes pressure to build within the fluid lines, one common method of detecting an occlusion within an infusion system includes monitoring the pressure of the fluid lines and activating an alarm when the back pressure exceeds a preset threshold. In such methods, a pressure sensor is placed in communication with a fluid line of the system. When an occlusion occurs in the fluid line, flow within the line is blocked or severely limited. As more fluid is added to the fluid pathway by the flow control device, the pressure within the fluid line increases. When the pressure exceeds a certain threshold, an alarm is activated to inform the patient or operator of the occlusion.

In infusions therapies where the fluid flowrate is relatively high, an occlusion causes a fairly quick increase of pressure within the fluid line, and the occlusion can be detected by a pressure sensor in a relatively short period of time. However, in infusion therapies where the flowrate is relatively low (for example, between about 0.1 ml/hr and about 10 ml/hr), pressure build-up within the fluid lines due to an occlusion can take a significant amount of time to reach the threshold level required for activating the occlusion alarm. Thus, when pressure of the fluid lines is used to detect occlusions in infusion system having low flowrates, there can be a considerable delay between the actual occurrence of an occlusion and the detection of the occlusion.

SUMMARY

The present disclosure relates to methods and devices for detecting an occlusion within an infusion system. In one embodiment, the infusion system includes a fluid source, a fluid flow control device, such as a fluid pump, and a fluid pathway. The fluid flow control device forces fluid from the fluid source, through the infusion circuit and into the patient. The infusion system also includes a flowrate sensor disposed along the fluid pathway to detect the flowrate through the infusion system. The flowrate sensor provides an analog output signal that expresses the fluid flowrate. The output signal can be in the form of volts, electric current or ticks of a counter. The flowrate sensor is in communication with a processing device, such as a microprocessor, which receives the output signal from the flowrate sensor. The processing device processes the output signal and compares the output signal to a threshold value to determine if an occlusion is present within the infusion system.

Use of the above device results in a method for detecting an occlusion within an infusion system. The method includes monitoring an output signal of a flowrate sensor that is disposed along the fluid pathway of an infusion system. The fluid path includes a pulsatile fluid flow flowing therethrough. A noise reduction filter, for example a ten second backward averaging filter, converts the output signal to obtain a filtered output signal. The filtered output signal is then compared to a preset threshold. If the filtered output signal falls below the threshold, an alarm is activated to signal to the user that an occlusion or other abnormal flow characteristic is present in the infusion system. In one embodiment, the desired threshold value is based on a baseline of the output signal, which is acquired or captured as fluid is initially flowed through the system. Optionally, the baseline can be converted to a baseline average by employing an averaging filter. In another embodiment, the threshold value is equal to the baseline average minus the standard deviation.

In another embodiment of the present disclosure, a method of detecting an occlusion within an infusion system is provided. The method includes monitoring an output signal from a flowrate sensor that is disposed along an infusion fluid pathway having a non-continuous or pulsatile flow of fluid therethrough. A data set that includes the output signal as a function of time is taken over a predetermined period of time. A noise rejection filter, such as a low-pass or high-pass frequency filter, filters the date to eliminate noise, such as patient or operator induced artifacts. Spectral analysis is then preformed on the filtered data set to determine the output signal strength in the frequency domain. The strength of the signal for a range or window of frequency that generally correlates with the frequency of the pulsatile fluid flow through the infusion system is calculated. In one embodiment, the strength of the signal of the frequency range is calculated by integrating the power-spectra in frequency domain for the range of frequency and computing the energy metric. The signal strength of the range can then be compared with an upper threshold value, a lower threshold value or both an upper and lower threshold value. If the signal strength is more than the upper threshold value, this indicates that there is an occlusion down stream of the flowrate sensor, and an alarm is activated indicating the same. If the signal strength is less than the lower threshold, this indicates that there is an occlusion upstream of the flowrate sensor, and an alarm is activated indicating the same.

Additional features and advantages are described herein, and will be apparent from, the following Detailed Description and the figures.

DETAILED DESCRIPTION

Figure 1:
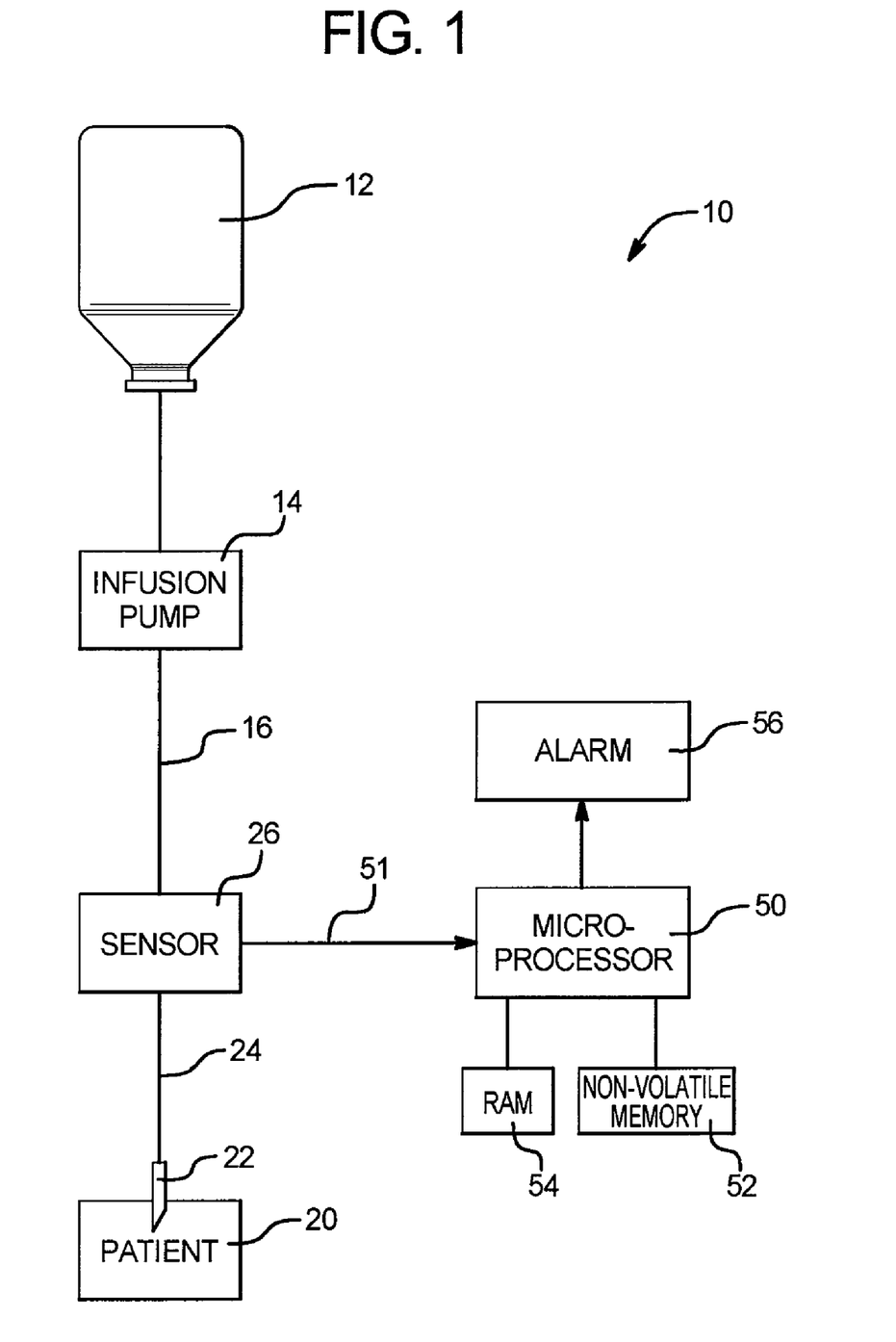
FIG. 1 is a schematic illustration of one embodiment of an infusion system of the present disclosure.

Referring now to the drawings and is particular to an infusion system 10 includes a fluid source 12, a fluid flow control device 14 and a fluid pathway 16. Fluid pathway 16 can include flexible tubing or other fluid flow conduits 18 that define a fluid path between fluid source 12 and a patient 20. A fluid administering device 22, such as a needle, cannula or catheter, is connected to the distal end 24 of fluid pathway 16 to administer fluid to the patient 20. Fluid flow control device 14 pumps or forces fluid from fluid source 12 through fluid pathway 16 into patient 20. In one embodiment, fluid flow control device 14 is a peristaltic or pulsatile infusion pump that operates on a regular cycle or frequency and provides a non-continuous or pulsatile fluid flow that pulsates at about the same frequency as the pumping frequency. In an alternate embodiment, flow control device 14 includes a valve that opens and closes in controlled time intervals to administer boluses of medication. Here, the flow can be driven by gravity, e.g., via a head height difference between source container 12 and a valving system between device 14 and patient 20. Alternatively a pressure producing devices such as a rubber-band around the container, a pressure cuff, or source container 12 being constructed out of an elastomeric material applies pressure on the fluid within container 12 to device the infusion fluid to patient 20.

Figure 2:
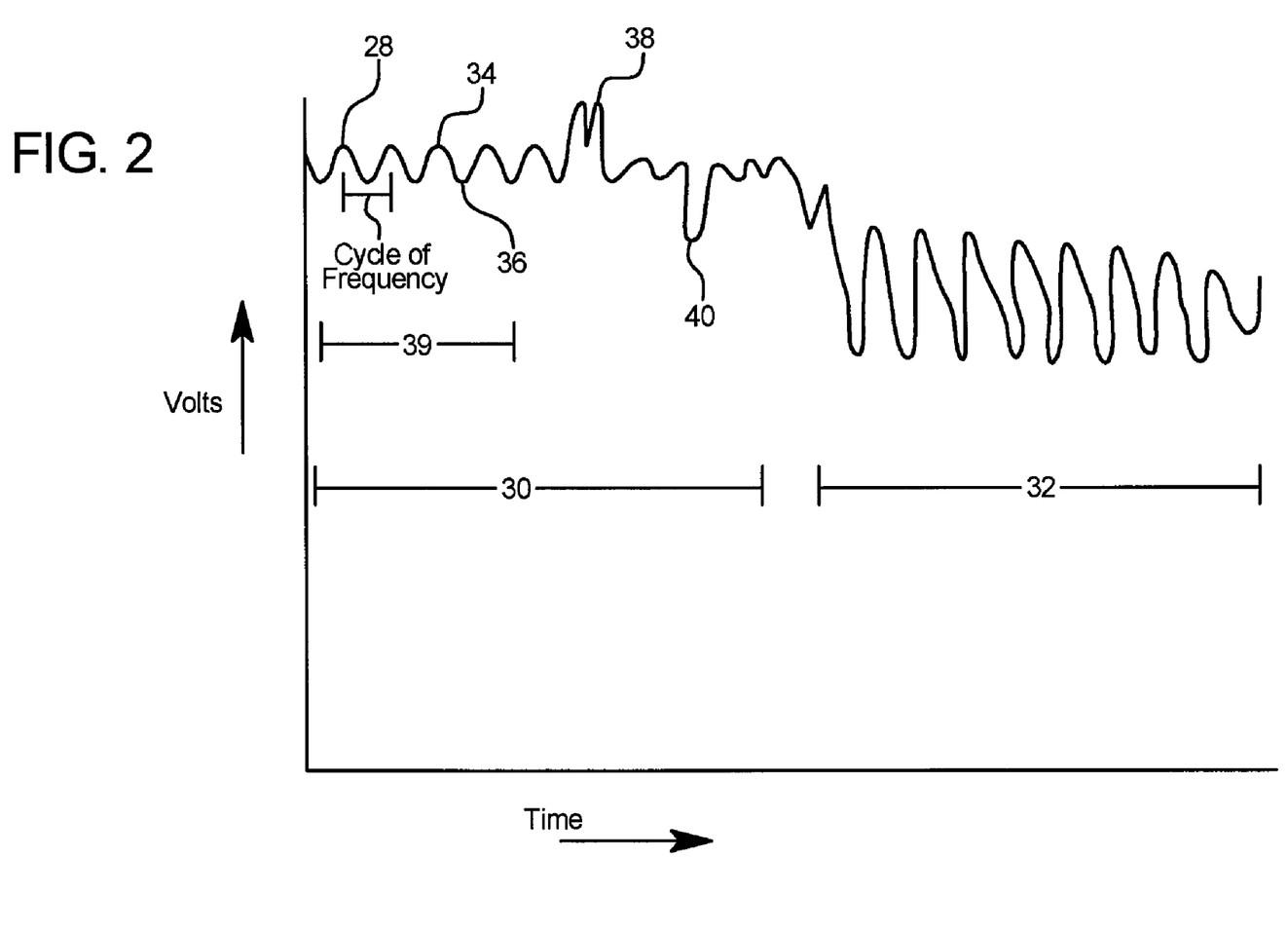
FIG. 2 is a graphical illustration of the output signal of the flowrate sensor versus time.

A flowrate sensor 26 is disposed along fluid pathway 16 at a location downstream of fluid flow control device 14. Flowrate sensor 26 detects and monitors the rate of fluid flow through the infusion system and produces a flowrate output signal. In one embodiment, the output signal is an analog output signal that can be expressed in volts, amperes or ticks of a counter. FIG. 2 illustrates one example of an analog output signal 28 from flowrate sensor 26, which monitors the flowrate of fluid through infusion system 10. In this example, output signal 28 from flowrate sensor 26 is measured in volts, and the signal is expressed in volts as a function of time. Additionally, the graph illustrates output signal 28 under normal flowrate conditions, generally designated at area 30, and flowrate conditions when an occlusion has occurred, generally designated at area 32.

Fluid flow device 14 can be a pulsatile or non-continuous infusion pump that operates at a certain pumping frequency. This type of pump creates a pulsatile fluid flow through the fluid pathway. The pulsatile fluid flow has a flowrate that varies at substantially the same frequency as the pumping frequency. Thus, as illustrated in FIG. 2, output signal 28 of flowrate sensor 26 also cycles at substantially the same frequency as the pumping frequency and includes peaks 34 and valleys 36. Patient and operator induced artifacts, such as movement by the patient, can also affect the flowrate and the flowrate sensor output signal. For example, these artifacts can affect the frequency and amplitude of the output signal as shown at 38 and 40.

The infusion system 10 can also include a processing device 50, such a microprocessor, which is configured to communicate with the flowrate sensor 26 to receive the output signal therefrom. Communication between the flowrate sensor 26 and the processing device 50 can be through any method, such as by a data cable 51 or through wireless communication. The processing device 50 can include non-volatile memory 52 that contains suitable software for carrying out the methods and processes described below. The processing device 50 can also include random access memory ("RAM") memory 54 that can be used as a work place for processing and storing data as necessary. An alarm 56 for signaling an occlusion is also in communication with the processing device. The alarm can be a visual display or an auditory indicator.

In one method of the present disclosure, the output signal of flowrate sensor 26 is analyzed and processed to quickly detect an occlusion within the infusion system and to reduce the number of false alarms. The method generally includes monitoring the output signal from a flowrate sensor and converting or filtering the signal with a noise reduction filter to suppress the peaks and valleys of the signal and the patient or operator induced artifacts. The filtered output signal is then compared against a predetermined threshold value to determine if an occlusion is located within the infusion system. In one embodiment, the predetermined threshold value is an expected value based on the pump setting. Optionally, the threshold value is calculated from a baseline of the output signal that is captured as fluid initially flows through the infusion circuit.

Figure 3:
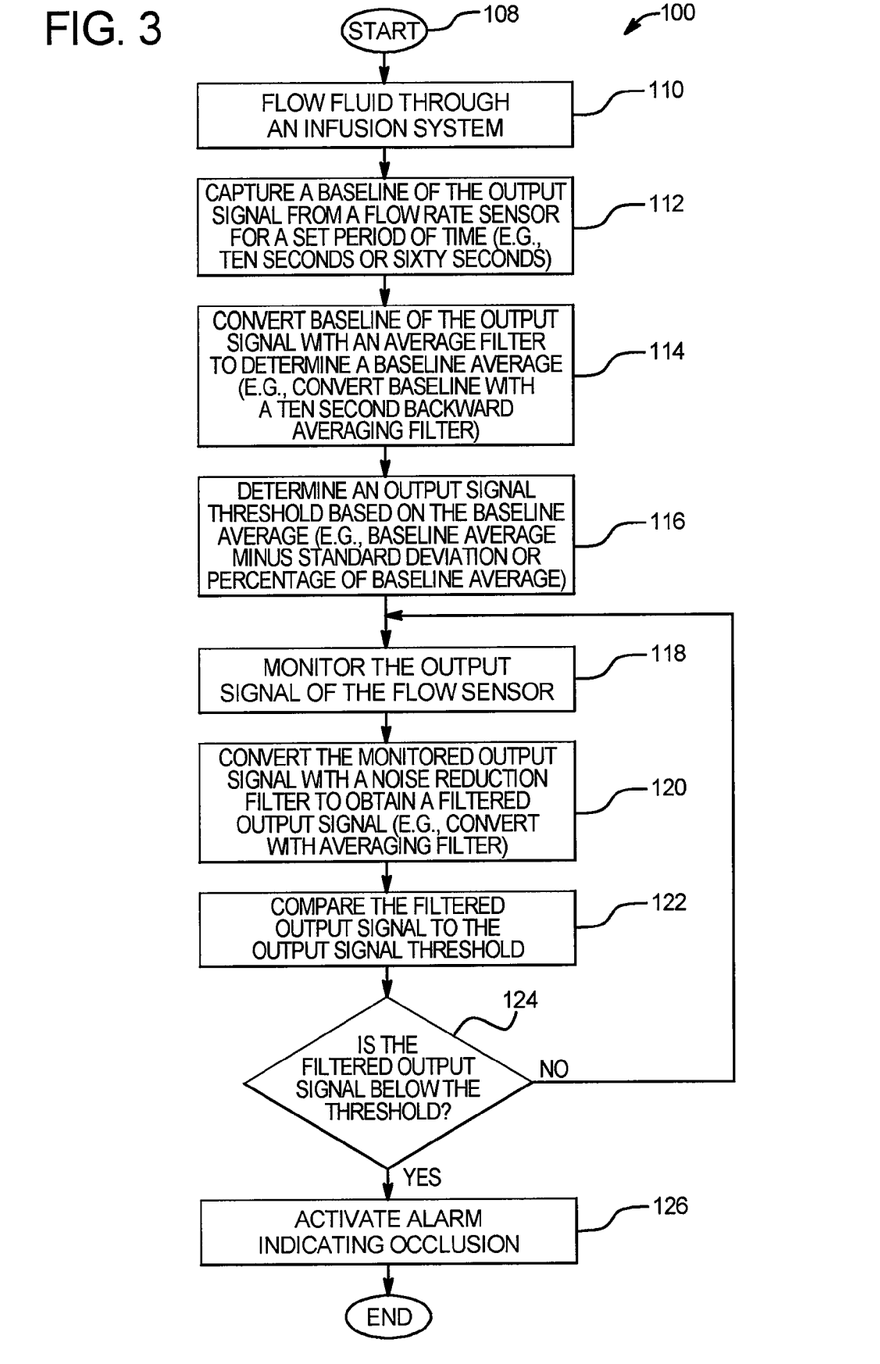
FIG. 3 is a flowchart illustrating one embodiment of an algorithm of the present disclosure for detecting an occlusion within an infusion system.

Referring now to FIG. 3, a flowchart showing one embodiment of a method 100 for detecting an occlusion within an infusion system is provided. The method 100 or portions of the method can be embodied in one or more software program, which is stored in one or more memory and executed by one or more processor. Additionally, the order of the steps may be changed, and some of the steps described may be optional.

Upon beginning method 100 at block 108, fluid is infused through the infusion system (pumped) at block 110. At block 112, a baseline of the output signal from the flowrate sensor is captured or acquired (e.g., taken and recorded) for a set period of time. The acquired baseline includes a set of data points including the strength of the output signal as a function of time. In one embodiment, the baseline is acquired as the infusion system is being primed. Alternatively, the baseline can be acquired as the fluid is initially infused into the patient. In one embodiment, the baseline is acquired for a time period between about ten seconds and about sixty seconds as the infusion system is being primed. When a pulsatile pump is used, the period of time in which the baseline is acquired can be based on a set number of pumping cycles of the pump.

After the baseline has been taken, turning to block 114, baseline 39 (shown in FIG. 2) is filtered or converted with a noise reduction or averaging filter to calculate a baseline average and standard deviation. In one embodiment, the baseline is filtered with a backward averaging filter. The backward averaging filter can be software that converts or filters the baseline with a backward averaging or moving averaging equation. One suitable filtering software is provided by National Instruments, Austin, Tex., under the name LabVIEW®.

In another embodiment, a ten second backward averaging filter is employed to obtain a baseline average. This filter converts the strength of the output signal of each baseline data point to an average of the data points acquired during the previous ten seconds. The collection of averaged data points forms the baseline average.

The averaging filter also can be other types of averaging filters such as a central averaging filter, a weighted averaging filter, a predictor-corrector type averaging filter or other averaging filter that is suitable for a plant model of the pump and delivery system. "Predictor-corrector" averaging filters typically include a method of predicting behavior of the 'plant' (in this case the infusion system), the corrector step then corrects this prediction using measured values.

Once the baseline average and standard deviation have been obtained, referring to block 116, a threshold value 41 (FIG. 4) is calculated. The threshold valve can be based on the baseline average, the standard deviation or both of these values. In one embodiment, the threshold value is the baseline average minus the standard deviation. In another embodiment, the threshold value is a percentage or a fraction of the baseline average. In yet another embodiment, the threshold value is not based on the baseline average, but instead is based on other factors, such as pump speed.

Figure 4:
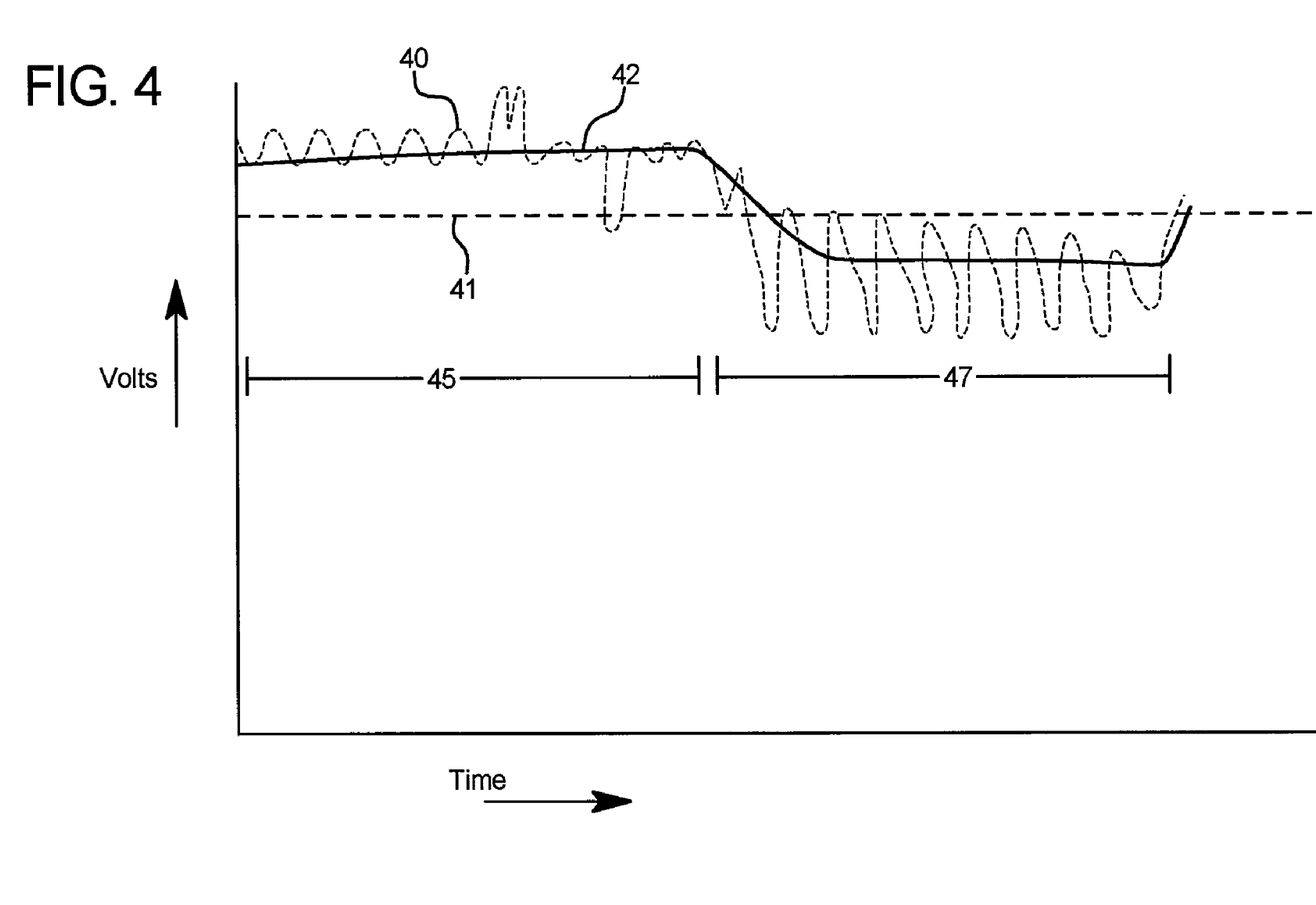
FIG. 4 is a graphical illustration of the filtered output signal versus time.

After the threshold value has been determined, at block 118, the output signal of the flowrate sensor is monitored. As discussed above, the output signal can be an analog signal. At block 120, the output signal is filtered or converted with a noise reduction filter, such as one of the averaging filters mentioned above. Converting the output signal with the noise reduction filter suppresses the peaks and valleys of the signal and also suppresses patient induced artifacts. For example, FIG. 4 illustrates a graphical comparison of output signal 28 (shown in dotted lines) and filtered output signal 42, which has been converted by an averaging filter (shown in a solid line). As can be seen by comparing output signal 28 and filtered output signal 42, applying a noise reduction filter to output signal 28 suppresses the peaks and valleys 34, 36 of signal 28 and the artifacts 38, 40.

At block 122, filtered signal 42 is then compared to threshold value 41. At block 124, method 100 determines if the filtered output signal is below the threshold value. If the filtered signal 42 is above the threshold value 41, for example at area 45 of the plot shown in FIG. 4, output signal 28 continues to be monitored, converted and compared to the threshold value. If filtered signal 42 falls below threshold value 41, for example at area 47 of the plot shown in FIG. 4, method 100 activates an alarm indicating that an occlusion has occurred, as shown in Block 126. The alarm can be any type of alarm, such as an auditory alarm or a visible alarm. Method 100 ends as seen at oval 128.

It should be appreciated that converting output signal 28 with a filter to suppress the peaks, valleys and artifacts of the signal reduces the chances of false alarms. For example, artifact 40 in FIG. 4 causes the output signal to fall below threshold level 41. If output signal 28 is not filtered, the artifact could trigger a false alarm. However, when the signal is converted with the filter, the artifact is suppressed, such that the level does not fall below the threshold, reducing the risk of false alarms.

In another embodiment of the present disclosure, when a pulsatile pump is used, an occlusion can be detected in an infusion system by comparing the strength of the flowrate sensor output signal at a selected range of frequency to a predetermined threshold level. As discussed above and referring again to FIG. 2, the pulsatile pump produces a pulsatile fluid flow having relatively the same frequency as the pumping frequency. The pulsatile fluid causes output signal 28 of the flowrate sensor to also have a frequency substantially similar to that of the pumping frequency. It has been found that an occlusion can be detected by comparing the signal strength of the output signal at the pumping frequency to an upper and/or lower preset threshold level. Further, the general location of the occlusion can also be determined depending on such comparison.

Figure 5:
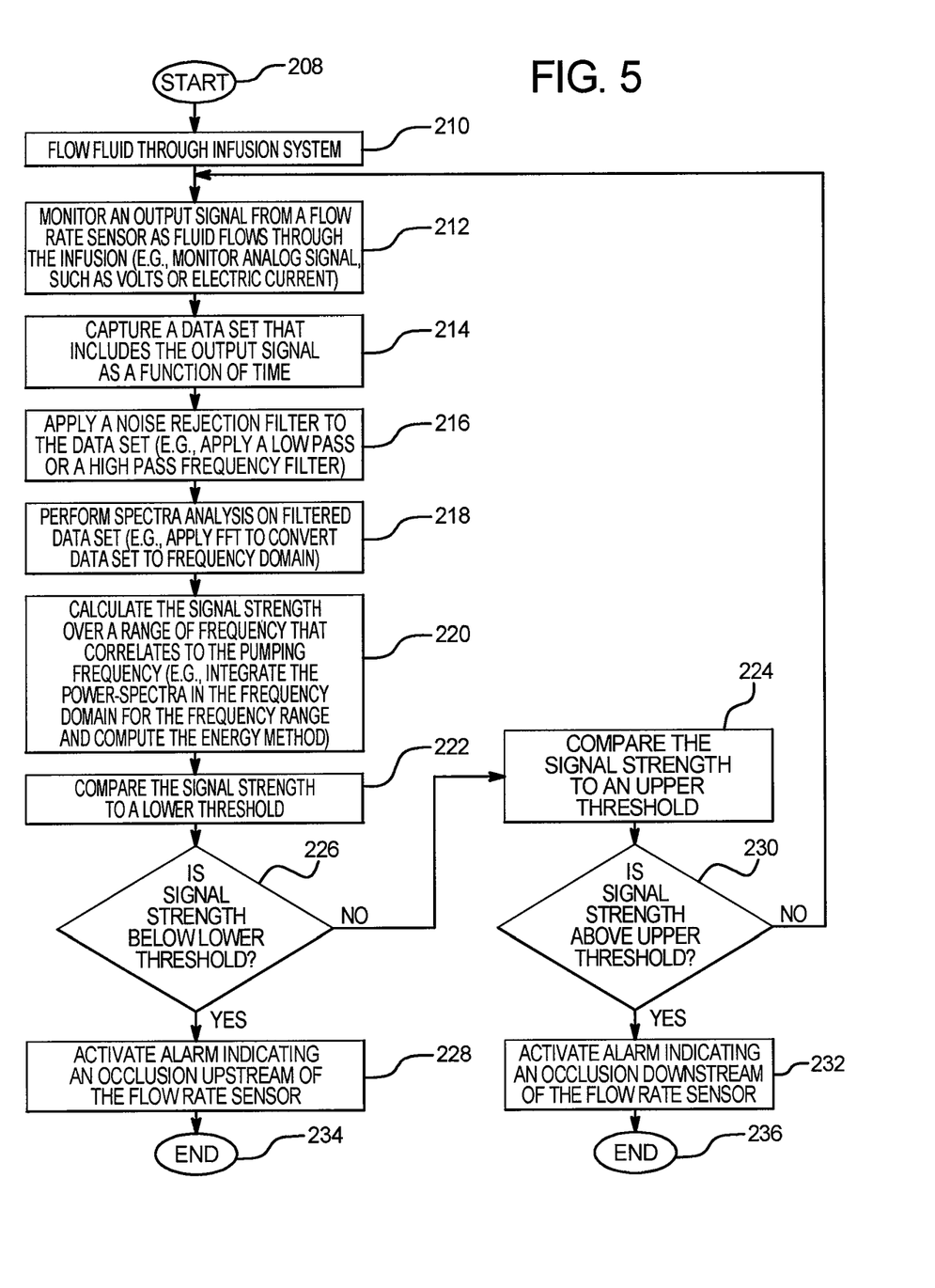
FIG. 5 is a flowchart illustrating another embodiment of an algorithm of the present disclosure for detecting an occlusion within an infusion system.

Referring now to FIG. 5, a flowchart showing one embodiment of a method 200 for detecting an occlusion based on the strength of the output signal within a range of frequency is provided. The method 200 or portions of the method can be embodied in one or more software program which is stored in one or more memory and executed by one or more processor. Further, the order of many of the steps may be changed, and some of the steps described may be optional.

Upon beginning method 200 at oval 208, fluid flows through the infusion system as seen at block 210. At block 212, the output signal from a flowrate sensor is monitored as the fluid is flowed through the infusion system. At block 214, a set of data is acquired or captured from the flowrate sensor for a predetermined period of time. The data set includes one of the types of output signals described above as a function of time.

At block 216, the data set is then filtered with a noise rejection filter to reduce noise that a patient or operator can cause, herein termed a patient or operator induced artifact. Such filters can include a low-pass frequency filter or a high-pass frequency filter. In one embodiment, the low-pass and high-pass frequency filters are provided in software that applies an algorithm to the data set. The algorithm filters out or attenuates (reduces the amplitude or frequency) frequency signals that are above a desired threshold and below a desired threshold. A low-pass frequency filter filters out or attenuates signals having frequencies that are higher than an upper threshold frequency. A high-pass frequency filter filters out or attenuates signals having frequencies below a lower threshold frequency. Software that includes such frequency filters can include the above mentioned LabVIEW® software.

After the filter has been applied, at block 218, power spectra analysis of the data set is preformed to determine the strength of the output signal per unit of frequency. Power spectra analysis transforms the data set from the time domain to the frequency domain signal, i.e., the date set is transformed from the output signal as a function of time to the strength of the signal as a function of frequency. Power spectra analysis can be performed by applying a Fourier transform algorithm to the filtered data set. In one embodiment, power spectra analysis is preformed on the filtered data set by analyzing the filtered data set with software, such as LabVIEW® software, which applies Fast Fourier Transform to the filtered data set.

At block 220, the signal strength of a frequency range that correlates to the pumping frequency is then calculated. In one embodiment, the frequency range is determined by identifying a pumping frequency, fp, and establishing a range based on the fraction of the pumping frequency, such as [fp−0.2*fp to fp+0.2*fp], or with a broader range of, e.g., [fp−0.35*fp to fp+0.35*fp] or by applying an asymmetric bias towards lower frequencies for signal search such a fp−alpha*fp to fp+beta*fp, in which alpha and beta are within [0:1] and alpha>beta. Characteristic values for alpha might be 0.35 or 0.5 and those for beta might be 0.1 or 0.2. The signal strength in one embodiment is calculated by integrating the power-spectra in the frequency domain (the area under the power curve in the frequency domain) and computing the energy metric. At blocks 222 and 224, the signal strength of frequency range is then compared to a lower threshold and a higher threshold, respectively. The upper and lower thresholds can be expected valves based on various factors, such as the pump setting, viscosity of fluid being infused, length and diameter of the tubing lines and patient back pressure.

At block 226, method 200 determines if the signal strength of the frequency range is below the lower threshold level. If the strength is below the lower threshold, method 200 assumes that there is an occlusion upstream of the flowrate sensor and activates an alarm indicating same, as illustrated in block 228. If the signal strength is above the lower threshold, the method 200 proceeds to block 224. The reason that signal strength below the threshold indicates an occlusion upstream of the flowrate sensor is that an occlusion upstream of the flowrate sensor reduces the flowrate of fluid flowing past the sensor. This reduction of flowrate reduces the strength of the signal, which causes the signal strength to fall below the threshold.

Referring to block 224, the strength of the signal of the frequency range is compared to an upper threshold. At block 230, method 200 determines if the signal strength is above the upper threshold. If the signal strength is above the upper threshold, method 200 assumes an occlusion has occurred downstream of the flowrate sensor and activates an alarm indicating same, as depicted in block 232. If the signal strength is below the upper threshold valve, then method 200 continues to monitor the signal as illustrated in block 212. Method 200 ends at oval 234 or oval 236. The reason that signal strength above a pre-set threshold indicates an occlusion downstream of the flowrate sensor is that when the occlusion is downstream of the flowrate sensor, the sensor detects the rebound effect of the fluid bouncing off of the occlusion as more and more fluid is pumped into the infusion circuit. This rebound effect increases the strength of the sensor signal.

It will be understood that the steps of method 200 of comparing the signal strength to a lower threshold level and/or an upper threshold level can include comparing the strength only to the lower threshold level, only to the upper threshold level or both the upper and lower threshold level. Additionally, the signal strength can be compared to the lower threshold first, the upper threshold first or both the lower and upper thresholds simultaneously.

For pumping systems that generate pulsatile and/or intermittent (sequences with flow on and off) flowrate waveforms, another detection mode is possible. If the flow sensor is capable of measuring bi-directional flow (that is flow proximal and distal, with outputs that are identifiable) and significant compliance does exist between the flow sensor and the downstream occlusion; the occlusion can be detected through virtua of identification of bi-directional flow, negative and positive flow, through the flow sensor. The compliance between the flow sensor and occlusion ensures that there is some volume change in the fluid delivery set and as a result positive flow through the flow sensor is detected in an early portion of the cycle. During a pump filling portion of the cycle, the pressurized volume will leak backward causing detection of negative flow. Repeated presence of positive and negative flows can be interpreted as a presence of an occlusion. Alternatively, one can include a drip chamber, flexible tube or compliance chamber in the fluid delivery set placed downstream of the flow sensor.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of detecting an occlusion for an infusion therapy comprising:
   obtaining a baseline output from a flowrate sensor;
   filtering the baseline output to form a filtered baseline output;
   determining an upper threshold value and a lower threshold value from the filtered baseline output;
   monitoring a therapy output of the flowrate sensor during the infusion therapy;
   filtering the therapy output to produce a filtered therapy output; and
   comparing the filtered therapy output to (i) the lower threshold value to determine if an occlusion is present upstream of the flowrate sensor, and (ii) the upper threshold value to determine if an occlusion is present downstream from the flowrate sensor.

2. The method of claim 1, which includes determining the occlusion if the filtered therapy output falls below the threshold value.

3. The method of claim 1, wherein monitoring the therapy output includes taking multiple sensor readings over multiple time intervals.

4. The method of claim 1, which includes obtaining the baseline output of the sensor before the infusion therapy begins.

5. The method of claim 1, which includes obtaining the baseline output of the sensor during a priming of the infusion therapy.

6. The method of claim 1, which includes obtaining the baseline output of the sensor as the infusion therapy begins.

7. The method of claim 1, which includes obtaining the baseline output of the sensor over a set number of cycles of a pump performing the infusion therapy.

8. The method of claim 1, which includes determining the threshold value based on at least one of: (i) a baseline average of the filtered baseline output and (ii) a standard deviation of the filtered baseline output.

9. The method of claim 1, wherein at least one of the filtering of the baseline output and the filtering of the therapy output includes using a filter of a type selected from the group consisting of: a backward averaging filter, a ten second backward averaging filter, a central averaging filter, a weighted averaging filter, and a predictor-corrector averaging filter.

10. A system configured to perform the method of claim 1.

11. An infusion system comprising:
    a fluid pathway between a fluid source and a patient;
    a flowrate sensor disposed along the fluid pathway; and
    a processing device in communication with the flowrate sensor, the processing device configured to (i) obtain a baseline output from the flowrate sensor; (ii) filter the baseline output to form a filtered baseline output, (iii) determine an upper threshold value and a lower threshold value from the filtered baseline output, (iv) monitor a therapy output of the flowrate sensor during the infusion therapy, (v) filter the therapy output to produce a filtered therapy output, and (vi) compare the filtered therapy output to (a) the lower threshold value to determine if an occlusion is present upstream of the flowrate sensor, and (b) the upper threshold value to determine if an occlusion is present downstream from the flowrate sensor.

* * * * *